US005484794A

United States Patent [19]
Bodick et al.

[11] Patent Number: 5,484,794
[45] Date of Patent: Jan. 16, 1996

[54] METHOD FOR TREATING ANXIETY

[75] Inventors: Neil C. Bodick, Indianapolis; Franklin P. Bymaster, Brownsburg; Walter W. Offen, Indianapolis; Harlan E. Shannon, Carmel, all of Ind.

[73] Assignee: Eli Lilly and Company, Indianapolis, Ind.

[21] Appl. No.: 336,589

[22] Filed: Nov. 9, 1994

[51] Int. Cl.⁶ .......................... A01N 43/90; A61K 31/44; C07D 453/02
[52] U.S. Cl. .................................................. 514/305
[58] Field of Search ............................................. 514/305

[56]        References Cited

U.S. PATENT DOCUMENTS

| 5,041,455 | 8/1991  | Sauerberg et al. | 514/342 |
| 5,043,345 | 8/1991  | Sauerberg et al. | 514/342 |
| 5,260,314 | 11/1993 | Sauerberg et al. | 514/305 |

FOREIGN PATENT DOCUMENTS

| 98113   | 1/1984 | European Pat. Off. . |
| 616807  | 9/1994 | European Pat. Off. . |
| 2264710 | 9/1993 | United Kingdom . |

OTHER PUBLICATIONS

Lukkari, P et al J. Chromatogr; A (1994) 674 (1–2) 241–6.
Njung'e, Kungu et al J. Psychopharmacol. (Oxford) (1993), 7(2), 173–80.

Primary Examiner—Paul J. Killos
Attorney, Agent, or Firm—MaCharri Vorndran-Jones; Robert A. Conrad; David E. Boone

[57]            ABSTRACT

The present invention provides a method for treating anxiety in humans using heterocyclic compounds.

1 Claim, No Drawings

METHOD FOR TREATING ANXIETY

BACKGROUND OF THE INVENTION

Extensive research has been conducted for a number of years directed toward the development of compounds capable of treating anxiety in humans that are safer to the user and which exhibit fewer side-effects. For example, several clinically established anxiolytic agents such as the barbituates, meprobamate and the benzodiazepines have numerous side effects such as potential for abuse and addiction or potentiation of the effects of ethanol. The mechanism of action of these compounds is believed to involve the GABA/benzodiazepine receptor complex in humans.

Buspirone is another compound which has been studied for the treatment of anxiety. The literature states that Buspirone interacts with reasonable potency only at the 5-$HT_{1A}$ and dopamine receptors. Alfred Goodman, et al., *Goodman and Gilman's The Pharmacological Basis of Therapeutics*, 8:482 (1990); Tompkins et al. *Research Communications in Psychology, Psychiatry, and Behavior*, 5:4, p. 338 (1980).

Sauerberg et al. in U.S. Pat. Nos. 5,043,345, 5,041,455 and 5,260314 disclose the compounds employed in the present invention as cholinergic compounds. As such, the compounds are taught to be useful in treating Alzheimer's disease, severe painful conditions, and glaucoma. There is no disclosure in the patents of using the compounds to treat anxiety.

The art has reported that compounds which act as agonists of the cholinergic muscarinic receptor can actually produce anxiety. See, Risch et al. *Psychopharmacol. Bull.*, 19:696–698 (1983), Nurnberger et al. *Psychiatry Res.*, 9:191–200 (1983), and Nurnberger et al. *Psychopharmacol. Bull.*, 17:80–82 (1982).

Surprisingly, we have discovered that a group of compounds having muscarinic cholinergic activity can be useful for treating anxiety. The present invention relates to a method of treating anxiety. More specifically, the invention provides a method of treating anxiety in humans using a tetrahydropyridine ori azabicyclic oxadiazole or thiadiazole compound. The activity of these compounds is believed to be based on agonist action at the m-1 muscarinic cholinergic receptor. As noted hereinbefore, the compounds employed in the method of the present invention are known. Methods of preparing the compounds, as well as pharmaceutical formulations containing the compounds, are taught by Sauerberg in U.S. Pat. Nos. 5,041,455, 5,043,345, and 5,260,314 herein incorporated by reference in their entirety.

SUMMARY OF THE INVENTION

The present invention provides a method for treating anxiety in humans comprising administering to a human in need thereof, an antianxiety dose of a compound of the Formula I

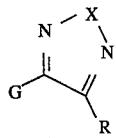

wherein
X is oxygen or sulphur;

R is hydrogen, amino, halogen, —CHO, —$NO_2$, —$OR^4$, —$SR^4$, —$SOR^4$, —$SO_2R^4$, $C_{3-7}$-cycloalkyl, $C_{4-8}$-(cycloalkylalkyl), —Z—$C_{3-7}$-cycloalkyl, and —Z—$C_{4-8}$-(cycloialkylalkyl) wherein $R^4$ is straight or branched $C_{1-15}$-alkyl, straight or branched $C_{2-15}$-alkenyl, straight or branched $C_{2-15}$-alkynyl, each of which is optionally substituted with one or more halogens, —$CF_3$, —CN, phenyl or phenoxy wherein phenyl or phenoxy is optionally substituted with halogen, —CN, $C_{1-4}$-alkyl, $C_{1-4}$-alkoxy, —$OCF_3$, —$CONH_2$ or —$CSNH_2$; or R is phenyl or benzyloxycarbonyl, each of which is optionally substituted with halogen, —CN, $C_{1-4}$-alkyl, $C_{1-4}$-alkoxy, —$OCF_3$, —$CONH_2$ or —$CSNH_2$; or R is —$OR^5Y$, —$SR^5Y$, —$OR^5ZY$, —$SR^5ZY$, —O—$R^4$—Z— $R^5$ or —S—$R^4$—Z—$R^5$ wherein Z is oxygen or sulphur, $R^5$ is straight or branched $C_{1-15}$-alkynyl, and Y is a 5 or 6 membered heterocyclic group containing one to four N, O or S atom(s) or a combination thereof, which heterocyclic group is optionally substituted at carbon or nitrogen atom(s) with straight or branched $C_{1-6}$-alkyl, phenyl or benzyl, or which heterocyclic group is optionally fused with a phenyl group; and G is selected from one of the following azabicyclic rings

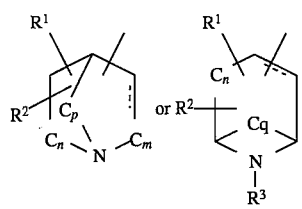

wherein the thiadiazole or oxadiazole ring can be attached at any carbon atom of the azabicyclic ring; $R^1$ and $R^2$ may be present at any position, including the point of attachment of the thiadiazole or oxadiazole ring, and independently are hydrogen, straight or branched $C_{1-5}$-alkyl, straight or branched $C_{2-5}$ alkenyl, straight or branched $C_{2-5}$-alkynyl, straight or branched $C_{1-10}$-alkoxy, straight or branched $C_{1-5}$-alkyl substituted with —OH, $OR^4$, halogen, —$NH_2$ or carboxy; $R^3$ is H, straight or branched $C_{1-5}$-alkyl, straight or branched $C_{2-5}$-alkenyl or straight or branched $C_{2-5}$-alkynyl; n is 0, 1 or 2; m is 0, 1 or 2; p is 0, 1 or 2; q is 1 or 2; and ═══ and is a single or double bond; or a pharmaceutically acceptable salt thereof.

DETAILED DESCRIPTION

It is to be understood that the invention extends to the use of each of the stereoisomeric forms of the compounds of the present invention as well as the pure diastereomeric, pure enantiomeric, and racemic forms of the named compounds.

The term "antianxiety dose", as used herein, represents an amount of compound necessary to prevent or treat a human susceptible to or suffering from anxiety following administration to such human. The active compounds are effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from anxiety, the compounds may also be administered by a variety of other routes such as the transdermal, parenterally, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed physical and/or mental condition once it has been established or alleviation of the characteristic symptoms of such condition.

As used herein the term "anxiety" refers to an anxiety disorder. Examples of anxiety disorders which may preferredly be treated using an effective amount of a named compound or pharmaceutically acceptable salt thereof include, but are not limited to: Panic Attack; Agoraphobia; Acute Stress Disorder; Specific Phobia; Panic Disorder; Psychoactive Substance Anxiety Disorder; Organic Anxiety Disorder; Obsessive-Compulsive Anxiety Disorder; Posttraumatic Stress Disorder; Generalized Anxiety Disorder; and Anxiety Disorder NOS.

Examples of anxiety disorders which may more preferredly be treated using an effective amount of a named compound or a pharmaceutically acceptable salt thereof include Panic Attack; Panic Disorder; Psychoactive Substance Anxiety Disorder; Organic Anxiety Disorder; Obsessive-Compulsive Anxiety Disorder; Posttraumatic Stress Disorder; Generalized Anxiety Disorder; and Anxiety Disorder NOS.

Examples of the anxiety disorders which are most preferredly treated using a named compound include Organic Anxiety Disorder; Obsessive-Compulsive Disorder; Posttraumatic Stress Disorder; Generalized Anxiety Disorder; and Anxiety Disorder NOS.

The named anxiety disorders have been characterized in the DSM-IV-R. *Diagnostic and Statistical Manual of Mental Disorders, Revised*, 4th Ed. (1994). The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic psychological conditions and that these systems evolve with medical scientific progress.

The compounds employed in the invention are not believed to act via the GABA/benzodiazepine, 5HT1A, or D1 receptor systems in humans. Rather, the activity of the present compounds as antianxiety agents is believed to be based upon modulation of muscarinic cholinergic receptors. However, the mechanism by which the present compounds function is not necessarily the mechanism stated supra., and the present invention is not limited by any mode of operation.

The following Examples are studies to establish the usefulness of the named compounds for treating anxiety.

EXAMPLE 1

Punished Responding

The antianxiety activity of the compounds employed in the method of the present invention is established by demonstrating that the compounds increase punished responding. This procedure has been used to establish antianxiety activity in clinically established compounds.

According to this procedure, the responding of rats or pigeons is maintained by a multiple schedule of food presentation. In one component of the schedule, responding produces food pellet presentation only. In a second component, responding produces both food pellet presentation and is also punished by presentation of a brief electric shock. Each component of the multiple schedule is approximately 4 minutes in duration, and the shock duration is approximately 0.3 seconds. The shock intensity is adjusted for each individual animal so that the rate of punished responding is approximately 15 to 30% of the rate in the unpunished component of the multiple schedule. Sessions are conducted each weekday and are approximately 60 min in duration. Vehicle or a dose of compound are administered 30 min to 6 hr before the start of the test session by the subcutaneous or oral route. Compound effects for each dose for each animal are calculated as a percent of the vehicle control data for that animal. The data are expressed as the mean±the standard error of the mean.

EXAMPLE 2

Monkey Taming Model

Further, the antianxiety activity of the compounds is established by demonstrating that the compounds are effective in the monkey taming model. Plotnikoff *Res. Comm. Chem. Path, & Pharmacol.*, 5: 128–134 (1973) described the response of rhesus monkeys to pole prodding as a method of evaluating the antiaggressive activity of a test compound. In this method, the antiaggressive activity of a compound was considered to be indicative of its antianxiety activity. Hypoactivity and ataxia were considered to be indicative of a sedative component of the compound. The present study is designed to measure the pole prod response-inhibition induced by a compound of this invention in comparison with that of a standard antianxiety compound such as diazepam as a measure of antiaggressive potential, and to obtain an indication of the duration of action of the compound.

Male and female rhesus or cynomologous monkeys, selected for their aggressiveness toward a pole, are housed individually in a primate colony room. Compounds or appropriate vehicle are administered orally or subcutaneously and the animals are observed by a trained observer at varying times after drug administration. A minimum of three days (usually a week or more) elapses between treatments. Treatments are assigned in random fashion except that no monkey receives the same compound two times consecutively.

Aggressiveness and motor impairment are graded by response to a pole being introduced into the cage as described in Table 1. The individuals responsible for grading the responses are unaware of the dose levels received by the monkeys.

TABLE 1

| Grading of Monkey Response to Pole Introduction | | |
|---|---|---|
| Response | Grade | Description |
| Attack | 2 | Monkey immediately grabbed and/or bit pole as it was placed at opening in cage. |

TABLE 1-continued

Grading of Monkey Response to Pole Introduction

| Response | Grade | Description |
|---|---|---|
| | 1 | Monkey grabbed and/or bit pole only after the tip was extended into the cage 12 inches or more. |
| | 0 | No grabbing or biting observed. |
| Pole Push | 2 | Monkey grabbed the pole to attack it or push it away. |
| | 1 | Monkey touched the pole only in attempting to avoid it or rode on the pole (avoidance). |
| | 0 | No pushing, grabbing or riding of the pole observed. |
| Biting | 2 | Monkey bit aggressively and frequently. |
| | 1 | Monkey bit weakly or infrequently |
| | 0 | No biting observed. |
| Ataxia | 2 | Monkey exhibited a marked loss of coordination. |
| | 1 | Slight loss of coordination observed. |
| | 0 | No effects on coordination observed. |
| Hypoactivity | 2 | Marked: Monkey was observed in a prone position. May or may not have responded by rising and moving away when experimenter approached. |
| | 1 | Slight: Monkey did not retreat as readily when experimenter approached |
| | 0 | None. |
| Antiaggression Activity of Drug Dose | + | Dose of drug was active in decreasing global assessment of aggressive behavior |
| | − | Dose of drug was not active in decreasing aggressive behavior |

EXAMPLE 3

Human Clinical Trials

Finally, the antianxiety activity of the named compounds can be demonstrated by human clinical trials. The study was designed as a double-blind, parallel, placebo-controlled multicenter trial. The patients were randomized into four groups, placebo and 25, 50, and 75 mg tid of test compound. The dosages were administered orally with food. Patients were observed at four visits to provide baseline measurements. Visits 5-33 served as the treatment phase for the study.

During the visits, patients and their caregivers were questioned and observed for signs of agitation, mood swings, vocal outbursts, suspiciousness, and fearfulness. Each of these behaviors are indicative of the effect of the test compound on an anxiety disorder.

For example, one test compound produced the following results:

| Behavioral Event | Placebo (N = 87) n (%) | 25 mg (N = 85) n (%) | 50 mg (N = 83) n (%) | 75 mg (N = 87) n (%) | p-Value |
|---|---|---|---|---|---|
| Agitation | 40 (46) | 34 (40) | 24 (29) | 20 (23) | .006 |
| Mood swings | 40 (46) | 25 (29) | 21 (25) | 28 (32) | .025 |
| Vocal Outbursts | 33 (38) | 29 (34) | 24 (29) | 11 (13) | .001 |
| Suspiciousness | 32 (37) | 23 (27) | 26 (31) | 7 (8) | <.001 |
| Fearfulness | 25 (29) | 28 (33) | 19 (23) | 13 (15) | .038 |

Treatment groups were compared with respect to the number and percent of patients who ever had the symptom during the double-blind portion of the study (visits 5 through 33), at a severity that was worse than during the baseline visits (1 through 4).

Preferred compounds for use in treating anxiety include:
3-CHLORO-3-(3-CHLORO-1,2,5-THIADIAZOL-4-YL)-1-AZABICYCLO[2.2.2]OCTANE;
3-(3-CHLORO-1,2,5-THIADIAZOL-4-YL)-3-HYDROXY-1-AZABICYCLO[2.2.2]OCTANE;
3-METHOXY-3-(3-METHOXY-1,2,5-THIADIAZOL-4-YL)-1-AZABICYCLO [2.2.2]OCTANE;
3-(3-METHOXY-1,2,5-THIADIAZOL-4-YL)-1-AZABICYCLO[2.2.2]OCT-2-ENE;
3-(3-HEXYLOXY-1,2,5-THIADIAZOL-4-YL)-1-AZABICYCLO[2.2.2]OCT-2-ENE;
3-HEXYLOXY-3-(3-HEXYLOXY-1,2,5-THIADIAZOL-4-YL)-1-AZABICYCLO[ 2.2.2]OCTANE;
3-(3-HEXYLOXY-1,2,5-THIADIAZOL-4-YL)-3-HYDROXY-1-AZABICYCLO[2.2.2]OCTANE;
3-(3-CHLORO-1,2,5-THIADIAZOL-4-YL)-1-AZABICYCLO[2.2.2]OCTANE;
3-(3-ETHOXY-1,2,5-THIADIAZOL-4-YL)-1-AZABICYCLO[2.2.2]OCTANE;
3-(3-PROPOXY-1,2,5-THIADIAZOL-4-YL)-1-AZABICYCLO[2.2.2]OCTANE;
3-(3-BUTOXY-1,2,5-THIADIAZOL-4-YL)-1-AZABICYCLO[2.2.2]OCTANE;
3-(3-PENTYLTHIO-1,2,5-THIADIAZOL-4-YL)-1-AZABICYCLO[2.2.2]OCTANE;
3-(3-ETHOXY-1,2,5-THIADIAZOL-4-YL)- 1-AZABICYCLO[2.2.2]OCTANE;
3-(3-HEXYLTHIO-1,2,5-THIADIAZOL-4-YL)-1-AZABICYCLO[2.2.2]OCTANE;
3-(3-(3-PHENYLPROPYLTHIO)-1,2,5-THIADIAZOL-4-YL)-1-AZABICYCLO[ 2.2.2]OCTANE;
3-(3-HEXYLTHIO-1,2,5-THIADIAZOL-4-YL)-1-AZABICYCLO[2.2.2]OCTANE;
3-(3-(4-CYANOBENZYLTHIO)-1,2,5-THIADIAZOL-4-YL)-1-AZABICYCLO[2.2.2]OCTANE;
EXO-6-(3-CHLORO-1,2,5-THIADIAZOL-4-YL)-1-AZABICYCLO[ 3.2.1]OCTANE;
ENDO-6-(3-CHLORO-1,2,5-THIADIAZOL-4-YL)-1-AZABICYCLO[ 3.2.1]OCTANE;
ENDO-6-(3-HEXYLTHIO-1,2,5-THIADIAZOL-4-YL)-1-AZABICYCLO[ 3.2.1]OCTANE;
ENDO-6-(3-(5-HEXENYLTHIO)-1,2,5-THIADIAZOL-4-YL)-1-AZABICYCLO[ 3.2.1]OCTANE;
ENDO-6-(3-BUTYLTHIO-1,2,5-THIADIAZOL-4-YL)-1-AZABICYCLO[ 3.2.1]OCTANE;
ENDO-6-(3-PENTYLTHIO-1,2,5-THIADIAZOL-4-YL)-1-AZABICYCLO[3.2.1]OCTANE;
ENDO-6-(3-ETHYLTHIO-1,2,5-THIADIAZOL-4-YL)-1-AZABICYCLO[ 3.2.1]OCTANE;
ENDO-6-(3-(3-PHENYLPROPYLTHIO)-1,2,5-THIADIAZOL-4-YL)-1-AZABICYCLO[ 3.2.1]OCTANE;
Endo-6-(3-(4-cyanobenzylthio)-1,2,5-thiadiazol-4-yl)-1-azabicyclo[3.2.1]octane;
Exo-6-(3-ethoxy-1,2,5-thiadiazol-4-yl)-1-azabicyclo[3.2.1]octane;

Endo-6-(3-ethoxy-1,2,5-thiadiazol-4-yl)-1-azabicyclo[3.2.1]octane;
Exo-3-(3-chloro-1,2,5-thiadiazol-4-yl)-1-azabicyclo[2.2.1]heptane;
Endo-3-(3-chloro-1,2,5-thiadiazol-4-yl)-1-azabicyclo[2.2.1]heptane;
Endo-3-(3-methoxy-1,2,5-thiadiazol-4-yl)-1-azabicyclo[2.2.1]heptane;
Exo-6-(3-hexylthio-1,2,5-thiadiazol-4-yl)-1-azabicyclo[3.2.1]octane;
Exo-6-(3-butylthio-1,2,5-thiadiazol-4-yl)-1-azabicyclo[3.2.1]octane;
Exo-6-(3-pentylthio-1,2,5-thiadiazol-4-yl)-1-azabicyclo[3.2.1]octane;
Exo-6-(3-ethylthio-1,2,5-thiadiazol-4-yl)-1-azabicyclo[3.2.1]octane;
Endo-3-(3-pentylthio-1,2,5-thiadiazol-4-yl)-1-azabicyclo[2.2.1]heptane;
Endo-3-(3-(3-phenylpropylthio)-1,2,5-thiadiazol-4-yl)-1-azabicyclo[2.2.1]heptane;
Endo-3-(3-butylthio-1,2,5-thiadiazol-4-yl)-1-azabicyclo[2.2.1]heptane;
Endo-3-(3-propylthio-1,2,5-thiadiazol-4-yl)-1-azabicyclo[2.2.1]heptane;
Exo-3-(3-pentylthio-1,2,5-thiadiazol-4-yl)-1-azabicyclo[2.2.1]heptane;
Exo-3-(3-hexylthio-1,2,5-thiadiazol-4-yl)-1-azabicyclo[2.2.1]heptane;
Exo-3-(3-propyithio-1,2,5-thiadiazol-4-yl)-1-azabicyclo[2.2.1]heptane;
Exo-3-(3-(3-phenylpropylthio)-1,2,5-thiadiazol-4-yl)-1-azabicyclo[2.2.1]heptane;
Exo-3-(3-butylthio-1,2,5-thiadiazol-4-yl)-1-azabicyclo[2.2.1]heptane;
3-Chloro-2-(3-ethoxy-1,2,5-thiadiazol-4-yl)-8-azabicyclo[3.2.1]oct-2-ene;
3-(3-Hexyloxy-1,2,5-thiadiazol-4-yl)-1-azabicyclo[2.2.2]octane;
3-(3-(6-Hexenyloxy)-1,2,5-thiadiazol-4-yl)-1-azabicyclo[2.2.2]octane;
3-(3-(3-Hexenyloxy)-1,2,5-thiadiazol-4-yl)-1-azabicyclo[2.2.2]octane;
-3(3-Pentyloxy-1,2,5-thiadiazol-4-yl)-1-azabicyclo[2.2.2]octane;
3-(3-Isopentyloxy-1,2,5-thiadiazol-4-yl)-1-azabicyclo[2.2.21]octane;
3-(3-Ethylthio-1,2,5-thiadiazol-4-yl)-1-azabicyclo[2.2.2]octane;
3-(3-Propylthio-1,2,5-thiadiazol-4-yl)-1-azabicyclo[2.2.2]octane;
-(3-Heptylthio-1,2,5-thiadiazoi-4-yl)-1-azabicyclo[2.2.2]octane;
Endo-6-(3-propylthio-1,2,5-thiadiazol-4-yl)-1-azabicyclo[3.2.1]octane;
Exo-6-(3-propylthio-1,2,5-thiadiazol-4-yl)-1-azabicyclo[3.2.1]octane;
Endo-3-(3-hexylthio-1,2,5-thiadiazoi-4-yl)-1-azabicyclo[2.2.1]heptane;
3-Chloro-2-(3-chloro-1,2,5-thiadiazol-4-yl)-8-azabicyclo[3.2.1]oct-2-ene;
Exo-6-(3-pentyloxy-1,2,5-thiadiazol-4-yl)-1-azabicyclo[3.2.1]octane;
Endo-6-(3-pentyloxy-1,2,5-thiadiazol-4-yl)-1-azabicyclo[3.2.1]octane;
4-Chloro-3-(3-chloro-1,2,5-thiadiazol-4-yl)-1-azabicyclo[3.3.1]non-3-ene;
4-Chloro-3-(3-propyloxy-1,2,5-thiadiazol-4-yl)-1-azabicyclo[3.3.1]non-3-ene;
4-Chloro-3-(3-pentyloxy-1,2,5-thiadiazol-4-yl)-1-azabicyclo[3.3.1]non-3-ene;
4-Chloro-3-(3-methoxy-1,2,5-thiadiazol-4-yl)-1-azabicyclo[3.3.1]non-3-ene;
4-Chloro-3-(1,2,5-thiadiazol-4-yl)-1-azabicyclo[3.3.1]non-3-ene;
(−) 3-(3-Butylthio-1,2,5-thiadiazol-4-yl)-1-azabicyclo[2.2.21]octane;
(+) 3-(3-Butylthio-1,2,5-thiadiazol-4-yl)-1-azabicyclo[2.2.21]octane;
3-(3-Amino-1,2,5-oxadiazol-4-yl)-1-azabicyclo[2.2.2]octane;
5-(3-Chloro-1,2,5-thiadiazol-4-yl)-1-azabicyclo[3.2.1]octane;
5-(3-Hexylthio-1,2,5-thiadiazol-4-yl)-1-azabicyclo[3.2.1]octane;
(5S,6S)-6-(3-butylthio-1,2,5-thiadiazol-4-yl)-1-azabicyclo[3.2.1]octane;
(5R,6R)-6-(3-propylthio-1,2,5-thiadiazol-4-yl)-1-azabicyclo[3.2.1]octane;
(5S,6S)-6-(3-propylthio-1,2,5-thiadiazol-4-yl)-1-azabicyclo[3.2.1]octane;
Exo-6-(3-butylsulfonyl-1,2,5-thiadiazol-4-yl)-1-azabicyclo[3.2.1]octane;
Exo-6-(3-(2,2,3,3,4,4,4-heptafluorobutyloxy)-1,2,5-thiadiazol-4-yl)-1-azabicyclo[3.2.1]octane;
Exo-6-(3-methoxy-1,2,5-thiadiazol-4-yl)-1-azabicyclo[3.2.1]octane;
Exo-6-(3-ethoxy-1,2,5-thiadiazol-4-yl)-1-azabicyclo[3.2.1]octane;
Exo-6-(3-propoxy-1,2,5-thiadiazol-4-yl)-1-azabicyclo[3.2.1]octane;
Exo-6-(3-butoxy-1,2,5-thiadiazol-4-yl)-1-azabicyclo[3.2.1]octane;
Exo-6-(3-pentyloxy-1,2,5-thiadiazol-4-yl)-1-azabicyclo[3.2.1]octane;
Exo-6-(3-hexyloxy-1,2,5-thiadiazol-4-yl)-1-azabicyclo[3.2.1]octane;
Exo-6-(3-isohexyloxy-1,2,5-thiadiazol-4-yl)-1-azabicyclo[3.2.1]octane;
Exo-6-(3-(2-butynyloxy)-1,2,5-thiadiazol-4-yl)-1-azabicyclo[3.2.1]octane;
Exo-6-(3-(3-(2-thienyl)-1-propylthio)-1,2,5-thiadiazol-4-yl)-1-azabicyclo[3.2.1] octane;
Endo-6-(3-(3-(2-thienyl)-1-propylthio)-1,2,5-thiadiazol-4-yl)-1-azabicyclo3.2.1]octane;
Endo-6-(3-(4,4,4-trifluorobutylthio)-1,2,5-thiadiazol-4-yl)-1-azabicyclo[3.2.1]octane;
Endo-6-(3-(6,6,6-trifluoro-1-hexytthio)-1,2,5-thiadiazol-4-yl)-1-azabicyclo[3.2.1]octane;
(5S,6S)-6-(3-butylsulfonyl-1,2,5-thiadiazol-4-yl)-1-azabicyclo[3.2.1] octane;
(5S,6S)-6-(3-(4,4,4-trifluoro-1-butylthio)-1,2,5-thiadiazol-4-yl)-1 -azabicyclo[3.2.1]octane;
3-(1,2,5-Thiadiazol-3-yl)-1-azabicyclo[2.2.2]octane;
Exo-3-(3-methylthio-1,2,5-thiadiazol-4-yl)-1-azabicyclo[2.2.1]heptane;
Exo-3-(3-ethylthio-1,2,5-thiadiazol-4-yl)-1-azabicyclo[2.2.1]heptane;
Endo-3-(3-(2-phenoxyethylthio)-1,2,5-thiadiazol-4-yl)-1-azabicyclo[2.2.1]heptane;
Endo-3-(3-(2-thienyl)propylthio-1,2,5-thiadiazol-4-yl)-1-azabicyclo[2.2.1]heptane;
Endo-3-(3-(2-phenylthio)ethylthio-1,2,5-thiadiazol-4-yl)-1-azabicyclo[2.2.1] heptane;
Exo-6-(3-methylthio-1,2,5-thiadiazol-4-yl)-1-azabicyclo[3.2.1]octane;

Exo-6-(3-heptylthio-1,2,5-thiadiazol-4-yl)-1-azabicyclo[3.2.1]octane;
Exo-6-(3-isohexylthio-1,2,5-thiadiazol-4-yl)-1-azabicyclo[3.2.1]octane;
Exo-6-(3-isopentylthio-1,2,5-thiadiazol-4-yl)-1-azabicyclo[3.2.1]octane;
Exo-6-(3-(4-cyanobutylthio)-1,2,5-thiadiazol-4-yl)-1-azabicyclo[3.2.1]octane;
Exo-6-(3-cyanomethylthio-1,2,5-thiadiazol-4-yl)-1-azabicyclo[3.2.1]octane;
Exo-6-(3-(2-cyanoethylthio)-1,2,5-thiadiazol-4-yl)-1-azabicyclo[3.2.1]octane;
Exo-6-(3-(3-cyanopropylthio)-1,2,5-thiadiazol-4-yl)-1-azabicyclo[3.2.1]octane;
Exo-6-(3-(4-cyanobenzylthio)-1,2,5-thiadiazol-4-yl)-1-azabicyclo[3.2.1]octane;
Exo-6-(3-(3-phenylpropylthio)-1,2,5-thiadiazol-4-yl)-1-azabicyclo[3.2.1]octane;
Exo-6-(3-(2-phenoxyethylthio)-1,2,5-thiadiazol-4-yl)-1-azabicyclo[3.2.1]octane;
Exo-6-(3-benzylthio-1,2,5-thiadiazol-4-yl)-1-azabicyclo[3.2.1]octane;
Endo-6-(3-(2-phenoxyethylthio)-1,2,5-thiadiazol-4-yl)-1-azabicyclo[3.2.1]octane;
Endo-6-(3-methylthio-1,2,5-thiadiazol-4-yl)-1-azabicyclo[3.2.1]octane;
Endo-6-(3-isopentylthio-1,2,5-thiadiazol-4-yl)-1-azabicyclo[3.2.1]octane;
Endo-6-(3-isohexylthio-1,2,5-thiadiazol-4-yl)-1-azabicyclo[3.2.1]octane;
Endo-6-(3-benzylthio-1,2,5-thiadiazol-4-yl)-1-azabicyclo[3.2.1]octane;
Endo-6-(3-cyanomethylthio-1,2,5-thiadiazol-4-yl)-1-azabicyclo[3.2.1]octane;
Endo-6-(3-(2-cyanoethyithio)-1,2,5thiadiazol-4-yl)-1-azabicyclo[3.2.1]octane
Endo-6-(3-(3-cyanopropylthio)-1,2,5-thiadiazol-4-yl)-1-azabicyclo[3.2.1]octane;
Endo-6-(3-(4-cyanobutyithio)-1,2,5-thiadiazol-4-yl)-1-azabicyclo[3.2.1]octane;
-Chloro-3-(3-butoxy-1,2,5-thiadiazol-4-yl)-1-azabicyclo[3.3.1]non-3-ene;
3-Chloro-3-(3-hexyloxy-1,2,5-thiadiazol-4-yl)-1-azabicyclo[3.3.1]non-3-ene;
3-(3-Butoxy-1,2,5-thiadiazol-4-yl)-1-azabicyclo[3.3.1]non-3-ene;
3-(3-Methoxy-1,2,5-thiadiazol-4-yl)-1-azabicyclo[3.3.1]non-3-ene;
3-(3-Propoxy-1,2,5-thiadiazol-4-yl)-1-azabicyclo[3.3.1]non-3-ene;
3-(3-Hexyloxy-1,2,5-thiadiazol-4-yl)-1-azabicyclo[3.3.1]non-3-ene;
3-(3-Isopentylthio-1,2,5-thiadiazol-4-yl)-1-azabicyclo[2.2.2]octane;
3-(3-(1-Methylpropylthio)-1,2,5-thiadiazol-4-yl)-1-azabicyclo[2.2.2]octane;
3-(3-Isobutylthio-1,2,5-thiadiazol-4-yl)-1-azabicyclo[2.2.2]octane;
3-(3-(2-Phenoxyethylthio)-1,2,5-thiadiazol-4-yl)-1-azabicyclo[2.2.2]octane;
3-(3-Cyanomethylthio-1,2,5-thiadiazol-4-yl)-1-azabicyclo[2.2.2]octane;
3-(3-(3-(2-Thienyl)propylthio)-1,2,5-thiadiazol-4-yl)-1-azabicyclo[2.2.2]octane;
3-(3-(4-Chlorobutylthio)-1,2,5-thiadiazol-4-yl)-1-azabicyclo[2.2.2]octane;
-3(3-Methylthio-1,2,5-thiadiazol-4-yl)-1-azabicyclo[2.2.2]octane;
3-(3-(1-Methyltetrazol-5-ylthio)butylthio-1,2,5-thiadiazol-4-yl)-1-azabicyclo[2.2.2]octane;
3-(3-(2-Methyl-1,3,4-thiadiazol-5-ylthio)butylthio-1,2,5-thiadiazol-4-yl)-1-azabicyclo[2.2.2]octane;
3-(3-(4-(2-Benzothiazolyl)thio)butylthio-1,2,5-thiadiazol-4-yl)-1-azabicyclo[2.2.2]octane;
3-(3-(4-Ethylbenzyloxy)-1,2,5-thiadiazol-4-yl)-1-azabicyclo[2.2.2]octane;
-3-(3-(3-(2-Thienyl)propoxy)-1,2, 5-thiadiazol-4-yl)-1-azabicyclo[2.2.2]octane;
(5R,6R)-6-(3-butylthio-1,2,5-thiadiazol-4-yl)-1-azabicyclo[3.2.1]octane;
3-(3-(N-(2-Ethylthio)phthalimide)-1,2,5-thiadiazol-4-yl)-1-azabicyclo[2.2.2]octane;
3-(3-(2-Methoxyethylthio)-1,2,5-thiadiazol-4-yl)-1-azabicyclo[2.2.2]octane;
3-(3-(2-(1,3-Dioxalan-2-yl)ethylthio)-1,2,5-thiadiazol-4-yl)-1-azabicyclo[2.2.2]octane;
3-(3-(4-Pyridylmethylthio)-1,2,5-thiadiazol-4-yl)-1-azabicyclo[2.2.2]octane;
3-(3-Cyclopropylmethylthio-1,2,5-thiadiazol-4-yl)-1-azabicyclo[2.2.2]octane;
3-(4-Fluorobenzylthio-1,2,5-thiadiazol-4-yl)-1-azabicyclo[2.2.2]octane;
Exo-6-(3-(4-fluorobenzylthio)-1,2,5-thiadiazol-4-yl)-1-azabicyclo[3.2.1]octane;
Exo-6-(3-(4-chlorobenzylthio)-1,2,5-thiadiazol-4-yl)-1-azabicyclo[3.2.1]octane;
Exo-6-(3-(4-methylbenzylthio)-1,2,5-thiadiazol-4-yl)-1-azabicyclo[3.2.1]octane;
Exo-6-(3-(4-trifluoromethoxybenzylthio)-1,2,5-thiadiazol-4-yl)-1-azabicyclo[3.2.1]octane;
Exo-6-(3-(4-thiocarbamylbenzylthio)-1,2,5-thiadiazol-4-yl)-1-azabicyclo[3.2.1]octane;
Exo-6-(3-(4-methylsulfonylbenzylthio)-1,2,5-thiadiazol-4-yl)-1-azabicyclo[3.2.1]octane;
Exo-6-(3-(5,5,5-trifluoropentylthio)-1,2,5-thiadiazol-4-yl)-1-azabicyclo[3.2.1]octane;
Exo-6-(3-(3,3,3-trifluoropropylthio)-1,2,5-thiadiazol-4-yl)-1-azabicyclo[3.2.1]octane;
Endo-6-(3-(4-trifluoromethoxybenzylthio)-1,2,5-thiadiazol-4-yl)-1-azabicyclo[3.2.1]octane;
Endo-6-(3-(4-methylbenzyithio)-1,2,5-thiadiazol-4-yl)-1-azabicyclo[3.2.1]octane;
Endo-6-(3-(4-fluorobenzylthio)-1,2,5-thiadiazol-4-yl)-1-azabicyclo[3.2.1]octane;
(5R,6R)-6-(3-propylsulfonyl-1,2,5-thiadiazol-4-yl)-1-azabicyclo[3.2.1]octane;
(5S,6S)-6-(3-propylsulfonyl-1,2,5-thiadiazol-4-yl)-1-azabicyclo[3.2.1]octane;
(5R,6R)-6-(3-(4-cyanobenzylthio)-1,2,5-thiadiazol-4-yl)-1-azabicyclo[3.2.1]octane;
5S,6S)-6-(3-(4-cyanobenzylthio)-1,2,5-thiadiazol-4-yl)-1-azabicyclo[3.2.1]octane;
(5S,6R)-6-(3-propylthio-1,2,5-thiadiazol-4-yl)-1-azabicyclo[3.2.1]octane;
(5R,6R)-6-(3-isohexyithio-1,2,5-thiadiazol-4-yl)-1-azabicyclo[3.2.1]octane;
(5S,6S)-6-(3-isohexylthio-1,2,5-thiadiazol-4-yl)-1-azabicyclo[3.2.1]octane;
(5R,6S)-6-(3-isohexylthio-1,2,5-thiadiazol-4-yl)-1-azabicyclo[3.2.1]octane;
(5S,6R)-6-(3-(4,4,4-trifluorobutylthio)-1,2,5-thiadiazol-4-yl)-1-azabicyclo[3.2.1]octane;
(5R,6S)-6-(3-(4,4,4-trifiuorobutylthio)-1,2,5-thiadiazol-4-yl)-1-azabicyclo[3.2.1]octane;
(5S,6R)-6-(3-(4-cyanobenzylthio)-1,2,5-thiadiazol-4-yl)-1-azabicyclo[3.2.1]octane;

(5R,6S)-6-(3-(4-cyanobenzylthio)-1,2,5-thiadiazol-4-yl)-1-azabicyclo[3.2.1]octane;
(5R,6R)-6-(3-(3,3,3-trifluoropropylthio)-1,2,5-thiadiazol-4-yl)-1-azabicyclo[3.2.1]octane;
(5R,6R)-6-(3-(3-(2-thienyl)propylthio)-1,2,5-thiadiazol-4-yl)-1-azabicyclo[3.2.1]octane;
(5R,6R)-6-(3-(4,4,4-trifluorobutylthio)-1,2,5-thiadiazol-4-yl)-1-azabicyclo[3.2.1]octane;
(5R,6S)-6-(3-(3,3,3-trifluoropropylthio)-1,2,5-thiadiazol-4-yl)-1-azabicyclo[3.2.1]octane;
or a pharmaceutically acceptable salt thereof.

Particularly preferred compounds for use in treating anxiety include:
3-(3-HEXYLTHIO-1,2,5-THIADIAZOL-4-YL)-1-AZABICYCLO[2.2.2]OCTANE;
3-(3-(3-PHENYLPROPYLTHIO)-1,2,5-THIADIAZOL-4-YL)-1-AZABICYCLO[2.2.2]OCTANE;
3-(3-CHLORO-1,2,5-THIADIAZOL-4-YL)-1-AZABICYCLO(2.2.2)OCTANE
(EXO (±))-6-(3-CHLORO-1,2,5-THIADIAZOL-4-YL)-1-AZABICYCLO(3.2.1)OCTANE
3-(3-ETHOXY-1,2,5-THIADIAZOL-4-YL)-1-AZABICYCLO(2.2.2)OCTANE
3-(3-PROPOXY-1,2,5-THIADIAZOL-4-YL)-1-AZABICYCLO(2.2.2)OCTANE
3-(3-BUTYLTHIO-1,2,5-THIADIAZOL-4-YL)-1-AZABICYCLO(2.2.2)OCTANE
3-(3-PENTYLTHIO-1,2,5-THIADIAZOL-4-YL)-1-AZABICYCLO(2.2.2)OCTANE
ENDO(±)-6-(3-ETHYLTHIO-1,2,5-THIADIAZOL-4-YL)-1-AZABICYCLO(3.2.1)OCTANE
ENDO (±)-6-(3-BUTYLTHIO-1,2,5-THIADIAZOL-4-YL)-1-AZABICYCLO(3.2.1)OCTANE
EXO(±)-6-(3-BUTYLTHIO-1,2,5-THIADIAZOL-4-YL)-1-AZABICYCLO(3.2.1)OCTANE
3-(3-(BUTOXY-1,2,5-THIADIAZOL-4-YL)-1-AZABICYCLO(2.2.2)OCTANE
EXO-3-(3-PROPYLTHIO-1,2,5-THIADIAZOL-4-YL)-1-AZABICYCLO(2.2.1)HEPTANE
EXO-3-(3-BUTYLTHIO-1,2,5-THIADIAZOL-4-YL)-1-AZABICYCLO(2.2.1)HEPTANE
ENDO-3-(3-BUTYLTHIO-1,2,5-THIADIAZOL-4-YL)-1-AZABICYCLO(2.2.1)HEPTANE
3-(3-ETHYLTHIO-1,2,5-THIADIAZOL-4-YL)-1-AZABICYCLO(2.2.2)OCTANE
3-(3-PROPYLTHIO-1,2,5-THIADIAZOL-4-YL)-1-AZABICYCLO(2.2.2)OCTANE
4-CHLORO-3-(3-PROPYLOXY-1,2,5-THIADIAZOL-4-YL)-1-AZABICYCLO(3.3.1)NON-2-ENE
3-(3-ISOPENTYLOXY-1,2,5-THIADIAZOL-4-YL)-1-AZABICYCLO(2.2.2)OCTANE
ENDO (±)3-(3-PROPYLTHIO-1,2,5-THIADIAZOL-4-YL)-1-AZABICYCLO( 3.2.1 )OCTANE
EXO (±)3-(3-PROPYLTHIO-1,2,5-THIADIAZOL-4-YL)-1-AZABICYCLO(3.2.1)OCTANE
–)3-(3-BUTYLTHIO-1,2,5-THIADIAZOL-4-YL)-1-AZABICYCLO(2.2.2)OCTANE
(+)3-(3-BUTYLTHIO-1,2,5-THIADIAZOL-4-YL)-1-AZABICYCLO(2.2.2)OCTANE
3-(3-CHLORO-1,2,5-THIADIAZOL-4-YL)-1-AZABICYCLO(2.2.2)OCTANE
(EXO (±))-6-(3-CHLORO-1,2,5-THIADIAZOL-4-YL)-1-AZABICYCLO(3.2.1)OCTANE
3-(3-ETHOXY-1,2,5-THIADIAZOL-4-YL)-1-AZABICYCLO(2.2.2)OCTANE
3-(3-PROPOXY-1,2,5-THIADIAZOL-4-YL)-1-AZABICYCLO(2.2.2)OCTANE
3-(3-BUTYLTHIO-1,2,5-THIADIAZOL-4-YL)-1-AZABICYCLO(2.2.2)OCTANE
3-(3-PENTYLTHIO-1,2,5-THIADIAZOL-4-YL)-1-AZABICYCLO(2.2.2)OCTANE
ENDO (±)-6-(3-ETHYLTHIO-1,2,5-THIADIAZOL-4-YL)-1-AZABICYCLO(3.2.1)OCTANE
ENDO (±)-6-(3-BUTYLTHIO-1,2,5-THIADIAZOL-4-YL)-1-AZABICYCLO(3.2.1)OCTANE
EXO (±)-6-(3-BUTYLTHIO-1,2,5-THIADIAZOL-4-YL)-1-AZABICYCLO(3.2.1)OCTANE
3-(3-(BUTOXY-1,2,5-THIADIAZOL-4-YL)-1-AZABICYCLO(2.2.2)OCTANE
EXO-3-(3-PROPYLTHIO-1,2,5-THIADIAZOL-4-YL)-1-AZABICYCLO(2.2.1)HEPTANE
3-(3-ETHYLTHIO-1,2,5-THIADIAZOL-4-YL)-1-AZABICYCLO(2.2.2)OCTANE
EXO-3-(3-BUTYLTHIO-1,2,5-THIADIAZOL-4-YL)-1-AZABICYCLO(2.2.1)HEPTANE
ENDO-3-(3-BUTYLTHIO-1, 2,5-THIADIAZOL-4-YL)-1-AZABICYCLO(2.2.1)HEPTANE
3-(3-ETHYLTHIO-1,2,5-THIADIAZOL-4-YL)-1-AZABICYCLO(2.2.2)OCTANE
3-(3-PROPYLTHIO-1,2,5-THIADIAZOL-4-YL)-1-AZABICYCLO(2.2.2)OCTANE
4-CHLORO-3-(3-PROPYLOXY-1,2,5-THIADIAZOL-4-YL)-1-AZABICYCLO(3.3.1)NON-2-ENE
3-(3-ISOPENTYLOXY-1,2,5-THIADIAZOL-4-YL)-1-AZABICYCLO(2.2.2)OCTANE
ENDO (±)3-(3-PROPYLTHIO-1,2,5-THIADIAZOL-4-YL)-1-AZABICYCLO(3.2.1)OCTANE
BIS-1,4-(3-(1-METHYL-1,2,5,6-TETRAHYDROPYRIDIN-3-YL)-1,2,5-THIADIAZOL-4-YL)BUTANEDITHIOL
EXO (±)3-(3-PROPYLTHIO-1,2,5-THIADIAZOL-4-YL)-1-AZABICYCLO(3.2.1)OCTANE
(–)3-(3-BUTYLTHIO-1,2,5-THIADIAZOL-4-YL)-1-AZABICYCLO( 2.2.2 )OCTANE
(+)3-(3-BUTYLTHIO-1,2,5-THIADIAZOL-4-YL)-1-AZABICYCLO(2.2.2.)OCTANE; AND
a pharmaceutically acceptable salt thereof.

More preferred compounds include the following:
3-(3-BUTYLTHIO-1,2,5-THIADIAZOL-4-YL)-1-AZABICYCLO(2.2.2)OCTANE
3-(3-PENTYLTHIO-1,2,5-THIADIAZOL-4-YL)-1-AZABICYCLO(2.2.2)OCTANE
ENDO (±)-6-(3-ETHYLTHIO-1,2,5-THIADIAZOL-4-YL)-1-AZABICYCLO( 3.2.1 )OCTANE
ENDO (±)-6-(3-BUTYLTHIO-1,2,5-THIADIAZOL-4-YL)- 1-AZABICYCLO(3.2.1)OCTANE
EXO (±)-6-(3-BUTYLTHIO-1,2,5-THIADIAZOL-4-YL)-1-AZABICYCLO(3.2.1)OCTANE
3-(3-PROPYLTHIO-1,2,5-THIADIAZOL-4-YL)-1-AZABICYCLO( 2.2.2)OCTANE; or
a pharmaceutically acceptable salt thereof.

Compound which are particularly preferred include:
3-(3-BUTYLTHIO-1,2,5-THIADIAZOL-4-YL)-1-AZABICYCLO(2.2.2)OCTANE; or a pharmaceutically acceptable salt thereof

We claim:

1. A method for treating anxiety in humans comprising administering to a human in need thereof, an antianxiety dose of a compound of Formula I

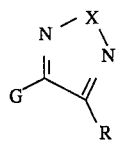

wherein

X is oxygen or sulphur;

R is hydrogen, amino, halogen, —CHO, —NO$_2$, —OR$^4$, —SR$^4$, —SOR$^4$, —SO$_2$R$^4$, C$_{3-7}$-cycloalkyl, C$_{4-8}$-(cycloalkylalkyl), -Z-C$_{3-7}$-cycloalkyl, and -Z-C$_{4-8}$-(cycloalkylalkyl) wherein R$^4$ is straight or branched C$_{1-15}$-alkyl, straight or branched C$_{2-15}$-alkenyl, straight or branched C$_{2-15}$-alkynyl, each of which is optionally substituted with one or more halogens, —CF$_3$, —CN, phenyl or phenoxy wherein phenyl or phenoxy is optionally substituted with halogen, —CN, C$_{1-4}$-alkyl, C$_{1-4}$-alkoxy, —OCF$_3$, —CONH$_2$ or —CSNH$_2$; or R is phenyl or benzyloxycarbonyl, each of which is optionally substituted with halogen, —CN, C$_{1-4}$-alkyl, C$_{1-4}$-alkoxy, —OCF$_3$, —CONH$_2$ or —CSNH$_2$; or R is —OR$^5$Y, —SR$^5$Y, —OR$^5$ZY, —SR$^5$ZY, —O—R$^4$—Z—R$^5$ or —S—R$^4$—Z—R$^5$ wherein Z is oxygen or sulphur, R$^5$ is straight or branched C$_{1-15}$-alkynyl, and Y is a 5 or 6 membered heterocyclic group containing one to four N, O or S atom(s) or a combination thereof, which heterocyclic group is optionally substituted at carbon or nitrogen atom(s) with straight or branched C$_{1-6}$-alkyl, phenyl or benzyl, or which heterocyclic group is optionally fused with a phenyl group; and G is selected from one of the following azabicyclic rings

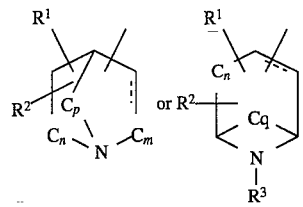

wherein the thiadiazole or oxadiazole ring can be attached at any carbon atom of the azabicyclic ring; R$^1$ and R$^2$ may be present at any position, including the point of attachment of the thiadiazole or oxadiazole ring, and independently are hydrogen, straight or branched C$_{1-5}$-alkyl, straight or branched C$_{2-5}$-alkenyl, straight or branched C$_{2-5}$-alkynyl, straight or branched C$_{1-10}$-alkoxy, straight or branched C$_{1-5}$-alkyl substituted with —OH, OR$^4$, halogen, —NH$_2$ or carboxy; R$^3$ is H, straight or branched C$_{1-5}$-alkyl, straight or branched C$_{2-5}$-alkenyl or straight or branched C$_{2-5}$-alkynyl; n is 0, 1 or 2; m is 0, 1 or 2; p is 0, 1 or 2; q is 1 or 2; and ---is a single or double bond; or a pharmaceutically acceptable salt thereof.

* * * * *